United States Patent [19]

Tsuruta et al.

[11] 4,217,130
[45] Aug. 12, 1980

[54] AGENTS FOR AND METHOD OF MODIFYING CITRUS FRUIT

[75] Inventors: Teruyuki Tsuruta, Fussa; Masanobu Kawai, Machida; Matsukuma Ikuo, Machida; Masayuki Teranishi, Machida; Nobuhiro Nakamizo, Machida, all of Japan

[73] Assignee: Kyowa Hakko Kogyo Co., Ltd., Tokyo, Japan

[21] Appl. No.: 954,210

[22] Filed: Oct. 24, 1978

[30] Foreign Application Priority Data

Oct. 29, 1977 [JP] Japan .................................. 52-130131

[51] Int. Cl.$^2$ .............................................. A01N 9/22
[52] U.S. Cl. ............................................ 71/95; 71/88; 260/326.45; 260/326.82; 260/326.83; 260/326.85; 544/141; 544/162

[58] Field of Search .................. 71/95, 44; 260/326.85

[56] References Cited

U.S. PATENT DOCUMENTS

| | | | |
|---|---|---|---|
| 3,439,018 | 4/1969 | Brookes et al. | 71/94 |
| 3,639,608 | 2/1972 | Adams et al. | 71/95 |
| 3,778,247 | 12/1973 | Pyne et al. | 71/95 |
| 3,804,853 | 4/1974 | D'Amico et al. | 71/95 |
| 4,065,291 | 12/1977 | Kobzina | 71/95 |

*Primary Examiner*—Glennon H. Hollrah
*Attorney, Agent, or Firm*—Fitzpatrick, Cella, Harper & Scinto

[57] ABSTRACT

Novel compounds are disclosed which are useful as agents capable, when applied to citrus tree, of modifying the metabolism and organic acid content of the citrus fruit.

2 Claims, No Drawings

AGENTS FOR AND METHOD OF MODIFYING CITRUS FRUIT

BACKGROUND OF THE INVENTION

The present invention relates generally to agents for improving the quality of citrus fruits and to a method of improving the quality of citrus fruits by application of such agents.

Chemicals capable of adjusting the metabolism of sugars and/or organic acids of citrus fruits are very useful, because they can improve the quality of citrus fruits and adjust the shipping time of the fruit. Chemicals capable of performing this function such as lead arsenate and naphthylacetic acids, are known. Lead arsenate has a pronounced effect of decreasing acidity of citrus fruits. However, lead arsenate is harmful to fruit trees and is residual in the fruit. Therefore, this agent is not preferable in view of the safety factor. Naphthylacetic acids also decrease the acidity in citrus fruit; but delay maturity of the fruit. This creates a problem in scheduled shipping time of the fruit, thus proving to be of little practical use.

As a result of various studies, it has been found that certain compounds as set forth below can increase or decrease the amount of organic acids in citrus fruits, when applied to the fruit trees without doing any harm to the fruit trees or having any adverse effect upon the maturity of the fruit.

SUMMARY OF THE INVENTION

In accordance with the present invention, the metabolism of citric fruit is modified by application of a modifying agent containing, as an active ingredient, at least one compound represented by the general formula (I): R-X-Y, wherein R represents a lower alkyl group, an alicyclic alkyl group or

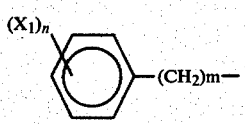

(wherein $X_1$ represents a hydrogen atom, a lower alkyl group, a lower alkoxy group, a halogen atom, or a nitro group, n is an integer of 1-5, m is 0 or 1, and when n is 2 or more, $X_1$ may be the same or different); X represents

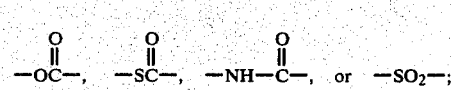

and Y represents

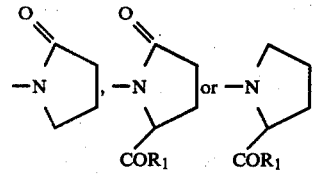

[wherein $R_1$ represents a hydroxyl group, a lower alkoxy group, or

(wherein $R_2$ and $R_3$ may be the same or different and are hydrogen atoms, lower alkyl groups, alicyclic alkyl groups, or aryl groups, or $R_2$ and $R_3$ form an oxa-hetero cycle with a nitrogen atom)].

The present invention also pertains to novel compounds included within the above general formula (I), with the exception of:

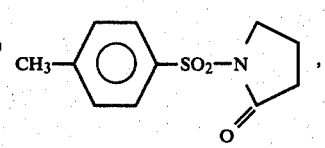

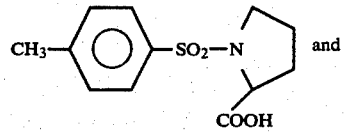

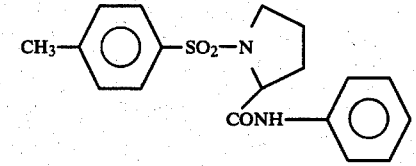

and the compounds wherein

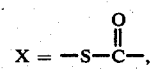

which are known.

The present invention is advantageous in that with an increase in the amount of organic acids in fruit, the preservability of the fruit after harvesting is improved; and with a decrease in the amount of organic acids, the ratio of sugar content to organic acid is raised and, therefore, the fruit can be harvested at an earlier time.

DESCRIPTION OF THE INVENTION

The compounds contemplated by the present invention, represented by the foregoing general formula (I), are set forth below in Table 1 by their structural formulae and melting points.

Table 1

| Compound number | Structural formula | Melting point (°C.) | Process* |
|---|---|---|---|
| 1 | CH₃–C₆H₄–SO₂–N(pyrrolidinone) | 140 | C |
| 2 | Cl–C₆H₄–SO₂–N(pyrrolidinone) | 144–145 | C |
| 3 | 2-Cl-C₆H₄–NHCO–N(pyrrolidinone) | 103–104 | B |
| 4 | C₆H₅–NHCO–N(pyrrolidinone-COOCH₃) | 91–92 | B |
| 5 | C₆H₅–NHCO–N(pyrrolidinone-CONHC₆H₅) | 210–211 | B |
| 6 | (CH₃)₂CH–NHCO–N(pyrrolidinone-COOH) (L) | 121.5–123 | B |
| 7 | C₆H₁₁–NHCO–N(pyrrolidinone-COOH) (L) | 97–100 | B |
| 8 | CH₃–C₆H₄–O–CO–N(pyrrolidine-COOH) (L) | 76–77 | A |
| 9 | O₂N–C₆H₄–O–CO–N(pyrrolidine-COOH) (L) | 73–74 | A |

Table 1-continued
| Compound number | Structural formula | Melting point (°C.) | Process |
|---|---|---|---|
| 10 | 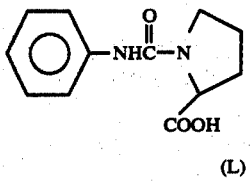 (L) | 168–169 | B |
| 11 | 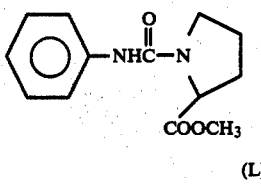 (L) | 46 | B |
| 12 | 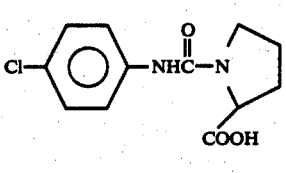 (L) | 171 | B |
| 13 | 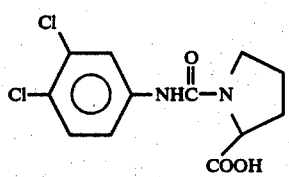 (L) | 163 | B |
| 14 | 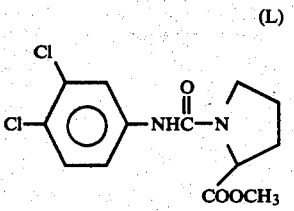 (L) | 90 | B |
| 15 | 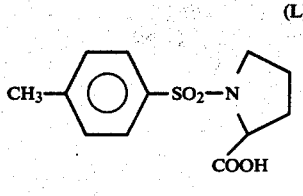 (L) | 57–59 | A |
| 16 | 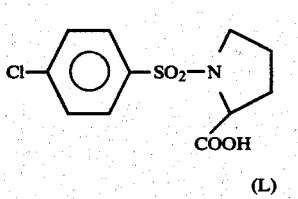 (L) | 97 | A |
| 17 | 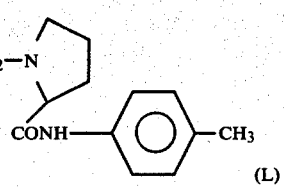 (L) | 113–114 | A |

Table 1-continued

| Compound number | Structural formula | Melting point (°C.) | Process* |
|---|---|---|---|
| 18 | CH₃–⟨phenyl⟩–SO₂–N⟨pyrrolidine⟩–CONH–⟨phenyl⟩ (L) | 140 | A |
| 19 | CH₃–⟨phenyl⟩–SO₂–N⟨pyrrolidine⟩–CONH–⟨3,4-dichlorophenyl⟩ (L) | 139 | A |
| 20 | ⟨2-chlorophenyl⟩–NHC(O)–N⟨pyrrolidine⟩–COOH (L) | 138 | B |
| 21 | ⟨3-chlorophenyl⟩–NHC(O)–N⟨pyrrolidine⟩–COOH (L) | 203 | B |
| 22 | Cl–⟨phenyl⟩–S(O)C–N⟨pyrrolidine⟩–COOCH₃ (L) | 90–91 | A |
| 23 | Cl–⟨phenyl⟩–S(O)C–N⟨pyrrolidine⟩–COOH (L) | 116–116.5 | A |
| 24 | Cl–⟨phenyl⟩–S(O)C–N⟨pyrrolidine⟩–CONH₂ (L) | 170.5–172 | A |
| 25 | Cl–⟨phenyl⟩–S(O)C–N⟨pyrrolidine⟩–CONHC₂H₅ (L) | 122–125 | A |

Table 1-continued

| Compound number | Structural formula | Melting point (°C.) | Process* |
|---|---|---|---|
| 26 | Cl–C₆H₄–S(=O)C–N(pyrrolidine)–CONH(C₂H₅)₂ (L) | 94–95 | A |
| 27 | Cl–C₆H₄–S(=O)C–N(pyrrolidine)–CON(morpholine) (L) | 81–83 | A |
| 28 | Cl–C₆H₄–CH₂S(=O)C–N(pyrrolidine)–CONH₂ (L) | 92–95 | A |
| 29 | Cl–C₆H₄–CH₂S(=O)C–N(pyrrolidine)–CONHC₂H₅ (L) | 90.2 | A |
| 30 | Cl–C₆H₄–CH₂S(=O)C–N(pyrrolidine)–CON(C₂H₅)₂ (L) | 68–69.5 | A |
| 31 | CH₃–C₆H₄–CH₂S(=O)C–N(pyrrolidine)–CONHC₂H₅ (L) | 86–87 | A |
| 32 | CH₃–C₆H₄–CH₂S(=O)C–N(pyrrolidine)–CON(C₂H₅)₂ (L) | 63–64 | A |
| 33 | CH₃–NHC(=O)–N(pyrrolidine)–COOH (L) | 135–136 | B |

Table 1-continued

| Compound number | Structural formula | Melting point (°C.) | Process* |
|---|---|---|---|
| 34 | C₂H₅—NHC(=O)—N(pyrrolidine)-COOH (L) | 131–133 | B |
| 35 | (CH₃)₃C—NHC(=O)—N(pyrrolidine)-COOCH₃ (L) | 76 | B |
| 36 | Cl-C₆H₄-SO₂—N(pyrrolidine)-COOCH₃ (L) | 105–106.5 | A |
| 37 | (CH₃)₃C—NHC(=O)—N(pyrrolidine)-COOH (L) | 111–112 | B |
| 38 | CH₃—NHC(=O)—N(pyrrolidinone) (L) | 126–127 | C |

*In the foregoing Table 1, A, B nd C indicate the general methods [A], [B], and [C] described hereinafter by which the compound may be prepared.

Among the above-mentioned compounds, compound numbers 1, 15 and 18 are known and are disclosed in Chemical Abstracts 51 11251e, Chemical Abstracts 49 14641c, and Chemical Abstracts 49 14640e, respectively. The remaining are believed to be novel compounds. Among the compounds represented by the general formula (I), those compounds wherein $$X = -S-\overset{O}{\underset{\|}{C}}-$$

are disclosed in the specification of Japanese Patent Application No. 61061/77.

The compounds used in the present invention may be prepared by the following general methods:

Process [A]

A compound represented by the general formula (I): R-X-Y [wherein R, X and Y have the same meanings as defined above] can be obtained by reaction of a halide represented by the general formula (II): R-X-Z (wherein R and X have the same meanings as defined above, and Z is a halogen atom) with a compound represented by the formula (III): H-Y (wherein Y has the same meaning as defined above). The process is indicated by the following reaction formula:

R—X—Z + H—Y ⟶ R—X—Y + HZ [Reaction A]
(II)    (III)        (I)

(a) As an example, when the compound represented by the general formula (II) has

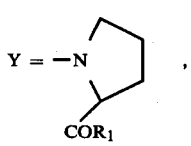

that is, in the case of a proline derivative, the procedure is as follows:

A compound represented by the general formula (III) is dissolved or suspended in water, an organic solvent, or a mixture thereof, and reacted with a halide represented by the general formula (II) with or without addition of a base, to obtain a compound represented by the general formula (I).

The proline derivatives represented by the general formula (II) are generally well-known compounds, or can be produced according to well-known methods. That is, when R₁ in

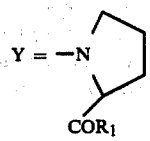

is a hydroxyl group, the compound represented by the general formula (III) is proline; when $R_1$ is a lower alkoxy group, the compound represented by the general formula (III) can be obtained by esterifying proline according to well-known esterification methods; when $R_1$ is

(wherein $R_2$ and $R_3$ have the same meanings as defined above), the compound represented by the general formula (II) can be obtained by condensing a proline, masked by a masking group such as a t-butyloxycarbonyl group, a benzyloxycarbonyl group, or the like according to the known methods employed in amino acids and peptide synthetic chemistry, with the corresponding amine, and then eliminating the masking group.

The proline used may be any of the optically active or optically inactive compounds.

Examples of a base used to promote the reaction [A] include organic bases such as triethylamine, dimethylaniline, N-methylmorpholine, pyridine, etc,; and inorganic bases such as sodium hydroxide, potassium hydroxide, sodium carbonate, potassium carbonate, sodium hydrogen carbonate, etc.

Organic solvents used in the reaction can be any of the organic solvents which do not take part in the reaction and inert organic solvents. Preferably, aromatic hydrocarbons, such as benzene, toluene, xylene, etc.; halogenated hydrocarbons, such as methylene chloride, chloroform, ethane dichloride, carbon tetrachloride, etc; esters, such as methyl acetate, ethyl acetate, etc,; ethers such as diethyl ether, dioxane, tetrahydrofuran, etc.; ketones such as acetone, methylethylketone, etc.; acetonitrile, dimethylformamide, etc. are used either alone or in mixture. The amount of the solvent used depends upon the reaction conditions, but usually 1 to 20 parts by weight of the solvent is used per part of starting material.

The reaction is carried out of a temperature range of $-50°$ C. to $100°$ C., preferably $-5°$ C. to $50°$ C., and is usually completed within 30 minutes to 24 hours.

The desired product can be isolated from the reaction mixture according to the ordinary isolation and purification procedures employed in the art of organic synthetic chemistry.

(b) When compounds represented by the general formula (III) wherein Y is

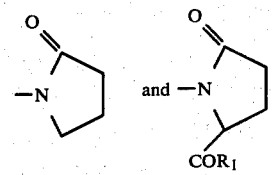

are used as the starting material, compounds represented by the general formula (I) can be obtained by conducting the reaction in the same manner as in the case of the proline derivative

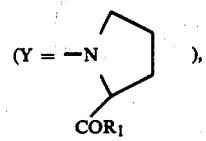

but these starting materials have less reactivity as compared with the proline derivatives, and thus are preferably treated with sodium hydride, sodium alkoxide, or the like in advance according to well-known procedures to undergo the reaction in the form of an alkali metal salt. In such case, the starting materials can be prepared according to ordinary well-known synthetic methods. As a solvent for the reaction, aromatic hydrocarbons such as benzene, toluene, xylene, etc.; esters such as methyl acetate, ethyl acetate, etc.; ethers such as diethyl ether, dioxane, tetrahydrofuran, etc.; dimethyl formamide, etc. can be used either alone or in mixture.

Process [B]

When X in the general formula (I) is

the compounds represented by the general formula (V) can be obtained by conducting the reaction in the same manner as in the case (a) or (b) of Process [A], except that an isocyanate derivative represented by the general formula (IV): R-NCO (wherein R has the same meaning as above) is used in Process [A] in place of the compound of the general formula (II). The process is indicated by the following reaction formula:

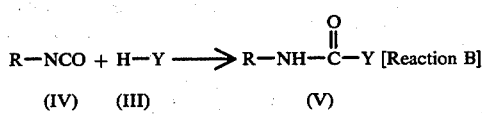

Process [C]

When $X = -SO_2-$ and

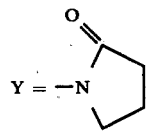

in the general formula (I), that is, when the compounds are

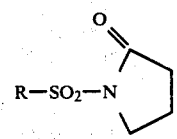

$R-SO_2NH(CH_2)_3COOH$ synthesized according to ordinary procedures in the art of peptide synthesis is subjected to cyclocondensation in the presence of an appropriate condensing agent to obtain a compound represented by

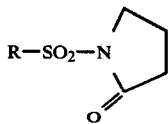

Dicyclohexyl carbodimide (DCC), ClCOOR$_4$ (wherein R$_4$ represents methyl, ethyl, sec-butyl, etc.), and the like are suitable condensing agents.

To promote the reaction, a base such as triethylamine, dimethylaniline, N-methylmorpholine, pyridine, N-methylpiperidine, etc. can be used. As the organic solvent used in the reaction, aromatic hydrocarbons such as benzene, toluene, xylene, etc.; halogenated hydrocarbons such as methylene chloride, chloroform, ethane dichloride, carbon tetrachloride, etc.; esters such as ethyl acetate, etc.; and the like can be used either alone or in mixture. The amount of the solvent used is usually 1 to 20 parts by weight per part of the starting material.

The reaction rapidly proceeds at a temperature range of −10° to 50° C., and is usually completed within 30 minutes to 24 hours.

The desired product can be isolated from the reaction mixture according to ordinary isolation and purification procedures employed in the art of organic synthetic chemistry.

Examples of the synthesis of certain specific compounds of the present invention are set forth below.

EXAMPLE A

In this example, 118 g of N-p-chlorophenylsulfonyl-γ-aminobutyric acid is suspended in 300 ml chloroform, and then 51 g of triethylamine is added in drops thereto in a water bath (about 20° C). A solution of ethyl chlorocarbonate (61.0 g) in chloroform (50 ml) is then added in drops to the reaction mixture for about 60 minutes with stirring while cooling the reaction mixture in an ice-salt bath (0°–5° C). After the addition, stirring is continued for two hours, and then the reaction mixture is admixed with 200 ml of ethyl acetate, and then washed twice with 100 ml of water. Then the reaction mixture is washed with 200 ml 1N hydrochloric acid, followed by two additional washings with 100 ml water, and finally dried over anhydrous sodium sulfate. The reaction mixture is filtered, and the filtrate is concentrated under reduced pressure. The resulting precipitate is recrystallized from ethanol, whereby 1p-chlorophenylsulfonylpyrolidone-2 (compound number 2; 105.7 g; mp 150°–151° C.) is obtained. Yield: 98.78%.

Elemental analysis Calculated: C:46.25, H:3.88, N:5.39%. Found: C:46.30, H:3.97, N:5.48%.

Compound numbers 1 and 38 are prepared in the same manner as described above.

EXAMPLE B

In this example, 14.3 g of methyl 2-pyrolidone-5-carboxylate and 10.1 g triethylamine are dissolved in 100 ml of ethyl acetate. Phenyl isocyanate (11.9 g) is added thereto, and the resulting solution is left standing at room temperature overnight. The reaction mixture is then filtered, and the filtrate is washed twice with 100 ml of 1N hydrochloric acid, and then three times with 100 ml water. Then, the filtrate is dried over anhydrous sodium sulfate, and then filtered. The filtrate is concentrated under reduced pressure, and the resulting viscous material is dissolved in 100 ml ether, admixed with 100 ml n-hexane, and recrystallized, whereby methyl 1-phenylcarbamoyl-2-pyrolidone-5-carboxylate (compound number 4; 17.5 g; mp 91°–92° C.) is obtained. Yield: 66.8%.

Elemental analysis Calculated: C: 59.53, H: 5.38, N: 10.68%. Found: C: 59.56, H: 5.40, N: 10.80%.

Compound numbers 3 and 5 are prepared in the same manner as described above.

EXAMPLE C

In this example, 117.0 g of L-proline and 0.7 g of sodium hydroxide are dissolved in 250 ml water, and then admixed with 250 ml acetonitrile. After cooling in an ice bath (5°–10° C.), a solution of 100 g isopropyl isocyanate dissolved in 100 ml acetonitrile is added in drops thereto for about 30 minutes with vigorous stirring. The solution is left standing at room temperature overnight, and then the reaction mixture is washed twice with 100 ml ethyl acetate. The aqueous layer is adjusted to pH 3–4 with 2N hydrochloric acid, and then evaporated to dryness under reduced pressure. The residue is admixed with 500 ml ethyl acetate, and heated to 70°–75° C. Insoluble materials are filtered off, and the filtrate is concentrated under reduced pressure. The resulting viscous material is admixed with 100 ml n-hexane, and crystallized, whereby n-isopropyl-carbamoyl-L-proline (compound number 6; 169.6 g; melting point 121.5°–123° C.) is obtained. Yield: 84.0%.

Elemental analysis Calculated (as C$_9$H$_{16}$N$_2$O$_3$): C: 53.98, H: 8.06, N: 13.99%. Found: C: 53.99, H: 8.16, N: 13.78%.

Compound numbers 7, 10, 12, 13, 20, 21, 33, 34 and 37 are prepared in the same manner as described above.

EXAMPLE D

In this example, 11.5 g L-proline and 8.0 g magnesium oxide are dissolved in 100 ml water, and then admixed with 60 ml ether. A solution of p-methylphenyl chloroformate [8.5 g; boiling point: 109°–110° C. (28–30 mmHg)] dissolved in 50 ml ether is added thereto, while cooling the mixture in an ice bath (5°–10° C.). After stirring for 30 minutes, the reaction solution is acidified by adding 60 ml concentrated sulfuric acid, and extracted three times with 60 ml ethyl acetate. The extract is washed three times with 40 ml 2N HCl and four times with 50 ml water, and then dried overnight over anhydrous sodium sulfate (30 g). After drying, the extract is filtered, and the filtrate is concentrated under reduced pressure. The resulting oily materials are admixed with 100 ml n-hexane, and left standing in a refrigerator (about −15° C.). The deposited crystals are filtered, and recrystallized from ethyl acetate-n-hexane (1:1 by volume), whereby p-methylphenyloxycarbonyl-L-proline (compound number 8; 9.25 g; mp: 76°–77° C.) is obtained. Yield: 74.3%.

Elemental analysis Calculated (as C$_{12}$H$_{15}$NO$_4$); C: 60.75, H: 6.37, N: 5.90%. Found: C: 60.67, H: 6.43, N: 5.83%.

Compound number 9 is prepared in the same manner as described above.

EXAMPLE E

In this example, 11.1 g of L-proline methyl ester hydrochloride and 6.7 g triethylamine are added to 100 ml chloroform, and 12.5 g of 3,4-dichlorophenyl isocyanate is added thereto with stirring. The resulting mixture is subjected to reaction overnight with stirring, and the reaction solution is then filtered. The filtrate is washed twice with 100 ml of 2N hydrochloric acid, and then four times with 100 ml water, dried over anhydrous sodium sulfate (30 g), and then filtered. The filtrate is concentrated under reduced pressure, and the resulting oily materials are recrystallized from about 200 ml ethanol, whereby N-3,4-dichlorophenylcarbamoyl-L-proline methyl ester (compound number 14; 18.8 g; m.p. 171° C.) is obtained. Yield: 79.5%.

Elemental analysis Calculated (as $C_{13}H_{14}N_2O_3Cl_2$): C: 49.23, H: 4.45, N: 8.83%. Found: C: 49.33, H: 4.47, N: 8.74%.

Compound numbers 11 and 35 are prepared in the same manner as described above.

EXAMPLE F

In this example, L-proline (11.5 g; 0.10 mole) and caustic soda (8.0 g; 0.2 moles) are dissolved in 100 ml water, and a solution of p-methylphenylsulfonyl chloride (20.9 g) dissolved in ether (80 ml) is added thereto with vigorous stirring under cooling in an ice bath (5°–10° C.). After reaction for about 5 hours, the reaction mixture is left standing, and the upper ether layer is removed. The remaining aqueous layer is admixed with 2N hydrochloric acid to adjust the pH to 3–4. After being left standing in a cool place (0°–5° C.), the deposited crystals are filtered off. The crystals are recrystallized from an aqueous 60% ethanol solution (about 200 ml), whereby p-methylphenylsulfonyl-L-proline (compound number 15; 20.1 g; m.p. 57°–59° C.) was obtained. Yield: 70%.

Compound number 16 is prepared in the same manner as described above.

EXAMPLE G

In this example, 8.07 g of N-p-methylphenylsulfonyl-L-proline and 3.03 g of triethylamine are dissolved in 100 ml ethyl acetate, and then dicyclohexyl carbodiimide (DCC; 6.18 g) is added thereto under ice cooling (5°–10° C.). The mixture is stirred for 20 minutes. After addition of 2.79 g aniline, the mixture is subjected to reaction at room temperature overnight with stirring. The deposited precipitate is filtered off, and the filtrate is washed three times with 100 ml water, twice with 100 ml 1N HCl, and then three times with 100 ml water. After drying over anhydrous sodium sulfate (about 30 g), the filtrate is concentrated under reduced pressure, and recrystallized from ethyl acetate-n-hexane (2:1 by volume), whereby N-p-methylphenylsulfonyl-L-proline anilide (compound number 18; 4.9 g; m.p. 140° C.) is obtained. Yield: 47.5%.

Elemental analysis Calculated: C: 59.99, H: 5.59, N: 7.77%. Found: C: 60.20, H: 5.68, N: 7.83%.

Compound numbers 17 and 19 are prepared in the same manner as described above.

EXAMPLE H

In this example, L-proline (3.5 g; 0.03 mole) and sodium carbonate (6.3 g; 0.075 mole) are dissolved in 90 ml water, and a solution of p-chlorophenylthiocarbonyl chloride (5.7 g; 0.033 mole) dissolved in 60 ml dioxane is added in drops thereto at 2°–10° C. under ice cooling for 15 minutes. After the addition, stirring is continued for five hours at 2°–5° C. After the completion of the reaction, the reaction solution is washed twice with 50 ml ether, and then the aqueous layer is acidified to pH 3–4 with concentrated hydrochloric acid, and separated oily substances are twice extracted with 50 ml ethyl acetate. The ethyl acetate layer is washed twice with 100 ml water, and then dried over sulfuric anhydride (about 10 g). The solvent is distilled off under reduced pressure, and the resulting syrupy material is admixed with 30 ml ether and 100 ml n-hexane, and left standing in a cool place (about −15° C.). The deposited crystals are filtered by suction, whereby white crystals of N-p-chlorophenylthiocarbonyl-L-proline (compound number 23; 5.0 g; m.p.: 116°–116.5° C.) is obtained. Yield: 65.9%.

Elemental analysis Calculated: C: 50.50, H: 4.20, N: 4.91%. Found: C: 50.63, H: 4.38, N: 4.94%.

EXAMPLE I

In this example, L-proline methyl ester hydrochloride (16.6 g; 0.1 mole) is dissolved in 100 ml chloroform, and the resulting solution is admixed with triethylamine (13.9 ml; 0.1 mole) under ice cooling (5°–10° C.) for 5 minutes. Then, 4-chlorophenylthiocarbonyl chloride (10.4 g; 0.05 moles) is added in drops at 2°–5° C. for 30 minutes. After stirring for three hours, the reaction solution is washed respectively with about 100 ml water, about 100 ml 2N hydrochloric acid and about 100 ml water, and then dried over anhydrous sodium sulfate (30 g). The solvent is distilled off under reduced pressure, and the resulting crystals are recrystallized from ethyl acetate (about 50 ml) and n-hexane (150 ml), whereby 4-chlorophenylthiocarbonyl-L-proline methyl ester (compound number 22; 18.0 g; m.p.: 90°–91° C.) is obtained. Yield: 60%.

Elemental analysis Calculated: C: 52.09, H: 4.70, N: 4.67%. Found: C: 52.21, H: 4.73, N: 4.76%.

Compound numbers 24–32 and 36 are prepared in the same manner as described above.

To modify the quality of citrus fruit according to the present invention, at least one of the compounds represented by the general formula (I) is sprayed upon citrus trees after appropriate dilution in a carrier. The compound can be applied as a solution, emulsion, suspension or dust produced according to ordinary methods for preparing plant growth regulators. Appropriate solid carriers include mineral powders such as clay, talc, kaolin, bentonite, diatomaceous earth, white carbon, and the like; and vegetable powders of soybean powder, wood dust, wheat flour, starch, fructose, etc. Appropriate liquid carriers include water; alcohols such as methanol, ethanol, ethyleneglycol, etc.; ketones such as acetone, methylisobutylketone, acetophenone, isophorone, etc.; ethers such as dioxane, tetrahydrofuran, ethyleneglycol, monobutyl ether, etc.; aromatic hydrocarbons such as benzene, toluene, xylene, methylnaphthalene, tetraline, etc.; kerosene, low or high boiling point petroleum fractions; polar solvents such as dimethyl formamide, dimethyl sulfoxide, acetonitrile, etc.

To improve the properties of preparations according to the invention and to increase the effect, various ionic and nonionic surfactants such as sodium laurylsulfate, sodium salts of higher alcohol sulfate esters, polyoxyethylene oleylether, or polymeric materials such as sodium alginate, methyl cellulose, carboxymethyl cellulose, polyvinyl alcohol, casein, etc. may be employed in combination with the carrier.

The preparation of the present invention can be used in mixture with other plant growth regulators as well as fungicides, miticides, insecticides, and the like.

The concentration of the active ingredients in the preparation is not especially critical, but in any formulation, the concentration is usually 100–2,000 ppm; and, upon application, it is preferably to spray the compound at a ratio of 300–600 L (active ingredient) per 10 acres of orchard having 60–80 fruit trees. The compound is sprayed once or twice in one season at any time during the fruiting period.

The carrier and other additives in a preparation can be used in such concentration ranges as used in ordinary plant growth regulators.

The effect of the agents of the present invention is illustrated by the following representative examples.

EXAMPLE 1

In this example, each of the compounds identified in Table 2 is dissolved in a small amount of methanol (20 mg/0.5 ml), and diluted with a 0.05% (w/v) aqueous solution of Gramine (trademark of a wetting agent made by Sankyo Seiyaku K.K.) to make up a concentration of 1000 ppm, in an aqueous solution.

The solution is sprayed on one-year old seedlings of Japanese summer orange at the fruiting period of the sprouts in early summer, so that the aqueous solution is thoroughly applied to the leaves. After one month, the treated leaves are collected, and the content of organic acid in the leaves is determined.

After extraction of the organic acids from the leaves by hot water, the organic acids are purified by ion exchange resin treatment using Amberlite CG-120 (made by Rohm & Haas), converted to a butyl ester, and then quantitatively determined by gas chromatography. The amount of organic acids in the fruit is proportionate to the amount of organic acids in the leaves (see "Shokucho" 10, No. 4, pages 14–19 (1976), or "Horticultural Utilization of Plant Growth Regulators", published by Seibundo-Shinko-sha Publishing Company, 1973), and thus the amount of organic acids in the leaves can serve as an index for indicating the amount of organic acids in the fruit.

As controls, lead arsenate and naphthylacetic acid (NAA) are used in place of the test compounds, and the amount of organic acids in the leaves is determined in the same manner as above. The results are set forth in Table 2 below.

Table 2

| Compound number | *A/B × 100(%) | Compound number | A/B × 100(%) | Compound number | A/B × 100(%) |
|---|---|---|---|---|---|
| Lead arsenate | 56 | 10 | 53 | 22 | 80 |
| NAA | 74 | 11 | 55 | 23 | 82 |
|  |  | 12 | 53 | 24 | 135 |
| 1 | 84 | 13 | 48 | 25 | 86 |
| 2 | 48 | 14 | 35 | 26 | 129 |
| 3 | 124 | 15 | 78 | 27 | 118 |
| 4 | 76 | 16 | 62 | 28 | 120 |
| 5 | 140 | 17 | 85 | 29 | 114 |
| 6 | 43 | 18 | 89 | 30 | 105 |
| 7 | 342 | 19 | 92 | 31 | 106 |
| 8 | 76 | 20 | 60 | 32 | 108 |
| 9 | 74 | 21 | 57 |  |  |

*A is the amount of organic acids in the treated leaves in terms of citric acid, and B the amount of organic acids in non-treated leaves in terms of citric acid.

EXAMPLE 2

In this example, ten parts by weight of the test compounds identified in Table 3, 5 parts by weight of sodium alkylbenzenesulfonate, 40 parts by weight of talc, and 45 parts by weight of bentonite are thoroughly pulverized and uniformly mixed in a mill to obtain a water dispersible powder. The water dispersible powder is diluted with a 0.05% aqueous solution of Gramine to make up an active ingredient concentration of 1,000 ppm, and sprayed on selected branches of 15 year-old, early ripening tangerine trees, at a rate of about 10 L per fruit tree to the same degree as in Example 1 (spraying date: July 17, 1976).

The fruit was harvested from the treated branches, and non-treated branches as control on Oct. 19, 1976, and the degree of coloring of the fruit, acidity of the fruit juice, and sugar content were measured. The amount of organic acids was determined by titration and calculated in terms of citric acid. The sugar content is measured by a refractometer and calculated in terms of glucose. The coloring is determined according to a ten-mark evaluation method. The results are given in Table 3.

Table 3

| Compound number | Coloring | Sugar content (P) | Acidity (g/100 ml) (Q) | Degree of sweetness (P/Q) |
|---|---|---|---|---|
| Control (non-treaed) | 5.5 | 9.4 | 1.22 | 7.74 |
| Lead arsenate | 6.0 | 9.7 | 1.09 | 8.9 |
| 2 | 6.0 | 9.6 | 1.05 | 9.14 |
| 4 | 6.0 | 9.8 | 1.15 | 8.52 |
| 6 | 5.5 | 9.6 | 0.96 | 10.0 |
| 10 | 5.0 | 9.7 | 1.09 | 8.9 |
| 14 | 5.0 | 9.5 | 0.90 | 10.56 |
| 23 | 6.0 | 9.9 | 1.18 | 8.39 |

EXAMPLE 3

In this example, the water dispersible mixture of Example 2 is diluted with a 0.5% aqueous solution of Gramine to make an active ingredient concentration of 2,000 ppm. The resulting solution is sprayed on 10-year old Japanese summer orange trees "Kawano" to the same degree as in Example 1 (spraying date: July 23, 1976). The fruit was harvested from the treated trees and non-treated trees as controls on Dec. 28, and the sugar content and acidity of the fruit juice was measured in the same manner as in Example 2. The results are given in Table 4.

Table 4

| Compound number | Sugar content (P) | Acidity (g/100 ml) (Q) | Degree of sweetness (P/Q) |
|---|---|---|---|
| Control (non-treated) | 9.8 | 2.55 | 3.84 |
| Lead arsenate | 9.1 | 1.76 | 5.17 |
| 2 | 9.7 | 2.02 | 4.80 |
| 4 | 9.8 | 2.25 | 4.36 |
| 6 | 9.8 | 1.63 | 6.01 |
| 10 | 9.7 | 2.07 | 4.69 |
| 14 | 9.6 | 1.80 | 5.33 |
| 23 | 9.8 | 2.29 | 4.28 |

EXAMPLE 4

In this example, forty parts by weight of the compounds identified in Table 5, 10 parts by weight of Sorbol 8067 (trademark of an anionic surfactant, made by Toho Kagaku Co., Ltd.), and 50 parts by weight of xylene were uniformly mixed and dissolved to obtain an emulsion. The emulsion is diluted with a 0.05% aqueous solution of Gramine to make up an active ingredient concentration of 500 ppm. The solution is sprayed on 15-year old, ordinary tangerine trees to the same degree as in Example 1 (spraying date: July 17, 1976). The fruit was harvested from the treated trees and non-treated trees on August 6, and the sugar content and acidity of fruit juice measured in the same manner as in Example 2. The results are given in Table 5.

Table 5

| Compound number | Sugar content (P) | Acidity (g/100 ml) (Q) | Degree of sweetness (P/Q) |
| --- | --- | --- | --- |
| Control (non-treated) | 7.1 | 4.11 | 1.73 |
| Lead arsenate | 7.2 | 3.36 | 2.14 |
| 2 | 7.3 | 3.63 | 2.01 |
| 4 | 7.3 | 3.85 | 1.90 |
| 5 | 7.0 | 4.87 | 1.44 |
| 6 | 7.1 | 2.99 | 2.37 |
| 10 | 7.0 | 3.66 | 1.91 |
| 14 | 7.2 | 3.31 | 2.18 |
| 16 | 7.2 | 3.72 | 1.94 |
| 23 | 7.3 | 3.88 | 1.88 |

What is claimed is:

1. A method of decreasing the organic acid content of citrus fruit which comprises applying to citrus trees bearing said fruit during the maturity thereof an effective amount of a compound represented by the formula

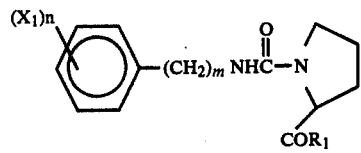

wherein $X_1$ represents a hydrogen atom, a lower alkyl group, a chlorine atom or a nitro group; n is an integer of 1–5; m is 0 or 1; $R_1$ is a hydroxyl group, a lower alkoxy group, or

wherein $R_2$ and $R_3$ may be the same or different and are a hydrogen atom, lower alkyl group, or an optionally substituted phenyl group; and when n is 2 or more, $X_1$ may be the same or different.

2. A method according to claim 1 wherein $X_1$ represents a hydrogen atom or a chlorine atom; n is an integer of 1–5; m is 0; $R_1$ is a hydroxyl group or a lower alkoxy group; and when n is 2 or more, $X_1$ may be the same or different.

* * * * *